US00PP22680P2

(12) United States Plant Patent
Senior

(10) Patent No.: US PP22,680 P2
(45) Date of Patent: Apr. 24, 2012

(54) ***BUDDLEJA* PLANT NAMED 'BURNCROSS'**

(50) Latin Name: ***Buddleja* hybrid**
Varietal Denomination: Burncross

(76) Inventor: John R. Senior, Richmond (GB)

( * ) Notice: Subject to any disclaimer, the term of this patent is extended or adjusted under 35 U.S.C. 154(b) by 0 days.

(21) Appl. No.: 12/925,455

(22) Filed: Oct. 21, 2010

(51) Int. Cl.
*A01H 5/00* (2006.01)

(52) U.S. Cl. ..... Plt./242
(58) Field of Classification Search ..... Plt./242
See application file for complete search history.

*Primary Examiner* — Susan McCormick Ewoldt
(74) *Attorney, Agent, or Firm* — C. A. Whealy

(57) ABSTRACT

A new and distinct cultivar of *Buddleja* plant named 'Burncross', characterized by its low growing, outwardly spreading and mounding plant habit; green and yellow green variegated leaves; violet blue-colored flowers; and good garden performance.

1 Drawing Sheet

Botanical designation: *Buddleja* hybrid.
Cultivar denomination: 'BURNCROSS'.

BACKGROUND OF THE INVENTION

The present invention relates to a new and distinct cultivar of *Buddleja* plant, botanically known as *Buddleja* hybrid and hereinafter referred to by the name 'Burncross'.

The new *Buddleja* plant originated from an open-pollination in an outdoor nursery in Moor House, North Yorks, United Kingdom, of an unnamed selection of *Buddleja* hybrid, not patented, as the female, or seed, parent with an unknown selection of *Buddleja* hybrid as the male, or pollen, parent. The new *Buddleja* plant was discovered and selected by the Inventor as a single flowering plant within the progeny of the stated open-pollination in a controlled outdoor nursery environment in Moor House, North Yorks, United Kingdom in July, 2000.

Asexual reproduction of the new *Buddleja* plant by cuttings in a controlled environment in Moor House, North Yorks, United Kingdom since July, 2000, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Burncross'. These characteristics in combination distinguish 'Burncross'as a new and distinct *Buddleja* plant:

1. Low growing, outwardly spreading and mounding plant habit.
2. Green and yellow green variegated leaves.
3. Violet blue-colored flowers.
4. Good garden performance.

Plants of the new *Buddleja* differ from plants of the female parent selection primarily in leaf coloration.

Plants of the new *Buddleja* can be compared to plants of *Buddleja* 'Harlequin', not patented. In side-by-side comparisons, plants of the new *Buddleja* and 'Harlequin' differed in the following characteristics:

1. Plants of the new *Buddleja* were more compact than plants of 'Harlequin'.
2. Plants of the new *Buddleja* and 'Harlequin' differed in leaf coloration.
3. Plants of the new *Buddleja* and 'Harlequin' differed in flower coloration.

Plants of the new *Buddleja* can also be compared to plants of *Buddleja davidii* 'Santana', disclosed in U.S. Plant Pat. No. 12,383. In side-by-side comparisons, plants of the new *Buddleja* and 'Santana' differed in the following characteristics:

1. Plants of the new *Buddleja* and 'Santana' differed in leaf coloration.
2. Plants of the new *Buddleja* and 'Santana' differed in flower coloration.

BRIEF DESCRIPTION OF THE PHOTOGRAPHS

The accompanying colored photographs illustrate the overall appearance of the new *Buddleja* plant showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Burncross' grown in a container.

The photograph at the top of the sheet is a close-up view of a typical inflorescence of 'Burncross'.

DETAILED BOTANICAL DESCRIPTION

The aforementioned photographs and following observations, measurements and values describe plants grown during the summer in one-gallon containers in an outdoor nursery in Lancaster, Pa. under commercial practice. During the production of the plants, day temperatures ranged from 21° C. to 38° C. and night temperatures ranged from 18° C. to 27° C. Plants were pinched one time and were six months old when the photographs and description were taken. In the following description, color references are made to The Royal Horticultural Society Colour Chart, 2007 Edition, except where general terms of ordinary dictionary significance are used.

Botanical classification: *Buddleja* hybrid 'Burncross'.

Parentage:

*Female, or seed, parent*.—Unnamed selection of *Buddleja* hybrid, not patented.

*Male, or pollen, parent*.—Unknown selection of *Buddleja* hybrid, not patented.

Propagation:

*Type*.—By cuttings.

*Time to initiate roots plant, summer*.—About 10 days at 21° C. to 25° C.

*Time to initiate roots plant, winter*.—About three months at 21° C. to 25° C.

*Time to produce a rooted plant, summer*.—About two months at 21° C. to 25° C.

*Time to produce a rooted plant, winter*.—About six months at 5° C. to 8° C.

*Root description*.—Medium in thickness, fibrous; close to 158B in color.

*Rooting habit*.—Freely branching; moderately dense.

Plant description:

*Plant form/habit*.—Deciduous perennial shrub; low growing, outwardly spreading and mounding plant habit; very broad inverted triangle; moderately vigorous growth habit.

*Plant height*.—About 27 cm.

*Plant width* (*spread*).—About 58 cm by 76 cm.

*Lateral branches*.—Quantity: About seven primary lateral branches with multiple secondary lateral branches per plant. Length: About 40 cm. Diameter: About 4 mm. Internode length: About 2.7 cm to 3 cm. Strength: Strong. Texture, developing stems: Pubescent. Texture, mature stems: Smooth, glabrous. Color, developing: Close to 145A. Color, mature: Close to N199B.

Foliage description:

*Arrangement*.—Opposite, simple.

*Length*.—About 5.8 cm.

*Width*.—About 1.8 cm.

*Shape*.—Elliptical.

*Apex*.—Acute.

*Base*.—Attenuate.

*Margin*.—Serrate.

*Texture, upper surface*.—Smooth, glabrous; slightly rugose.

*Texture, lower surface*.—Pubescent, lanulose; slightly rugose.

*Venation pattern*.—Pinnate; arcuate and reticulate.

*Color*.—Developing leaves, upper surface: Random sectors of close to 137A, 148C and 150D. Developing leaves, lower surface: Random sectors of close to 147C, 147D and 145D. Fully expanded leaves, upper surface: Random sectors of close to 137A, 146D and 150D; venation, close to 147B. Fully expanded leaves, lower surface: Random sectors of close to 148B, 147D and 149D; venation, close to 147C.

*Petiole*.—Length: About 4 mm. Diameter: About 1.5 mm. Texture, upper and lower surfaces: Pubescent. Color, upper and lower surfaces: Close to 146D.

Flower description:

*Flower type and flowering habit*.—Single small salver-form flowers arranged on terminal panicles; flowers face mostly outwardly; panicles relatively short and roughly conical in shape; freely flowering habit with about 102 flowers per inflorescence and about 14 inflorescences per plant.

*Fragrance*.—Faintly fragrant; sweet, violet-like.

*Natural flowering season*.—Continuously flowering throughout the late summer into the autumn in Pennsylvania; plants begin flowering about 12 to 13 weeks after planting.

*Postproduction longevity*.—Flowers last about five days on the plant; flowers persistent.

*Flower buds*.—Height: About 1.1 cm. Diameter: About 3 mm. Shape: Oblong. Color: Close to 97A.

*Inflorescence length*.—About 4.8 cm.

*Inflorescence diameter*.—About 2.7 cm.

*Flower diameter*.—About 5 mm.

*Flower depth*.—About 1.1 cm.

*Flower throat diameter*.—Close to 1 mm.

*Flower tube length*.—Close to 8 mm.

*Flower tube diameter*, at the base.—Close to 1.5 mm.

*Petals*.—Quantity per flower: Typically four in a single whorl; petals fused into a narrow tube. Lobe length: About 3 mm. Lobe width: About 2.5 mm. Shape: Roughly spatulate. Apex: Obtuse. Margin: Erosulate; slightly crinkled. Texture, upper surface: Smooth, glabrous. Texture, lower surface: Scattered pubescence. Texture, throat: Pubescent. Texture, tube: Scattered pubescence. Color: Developing petals, upper surface: Close to 92A. Developing petals, lower surface: Close to 91B. Fully expanded petals, upper surface: Close to 91A; towards the throat, a small ring, close to 158B; venation, close to 91A. Fully expanded petals, lower surface: Close to 91B, venation, close to 91B. Throat: Close to 163A; venation, close to 163A. Tube: Close to 91C, venation, close to 91C.

*Sepals*.—Quantity per flower: Typically four in a single whorl, fused towards the base into a short tube. Length: About 4 mm. Width: About 1 mm. Shape: Lanceolate. Apex: Acute. Margin: Entire. Texture, upper surface: Smooth, glabrous. Texture, lower surface: Pubescent. Color, upper surface: Close to 145A. Color, lower surface: Close to 148C.

*Peduncles*.—Length: About 1.4 cm. Diameter: About 1 mm. Strength: Moderately strong. Texture: Pubescent. Color: Close to 145B.

*Pedicels*.—Length: About 2 mm. Diameter: Less than 1 mm. Angle: About 45° from vertical. Strength: Moderately strong. Texture: Pubescent. Color: Close to 145B.

*Reproductive organs*.—Stamens: Quantity per flower: Typically four; filaments adnate to the corolla throat. Filament length: About 2.5 mm. Filament color: Close to 145D. Anther shape: Lanceolate. Anther length: About 1 mm. Anther color: Close to 194D. Pollen amount: None observed. Pistils: Quantity per flower: One. Pistil length: About 3 mm. Stigma shape: Oval. Stigma color: Close to 194A. Style length: About 1 mm. Style color: Close to 194D. Ovary color: Close to 145B.

*Seed/fruit*.—Seed and fruit development have not been observed.

Disease/pest resistance:

Plants of the new *Buddleja* have been not been observed to be resistant to pathogens and pests common to *Buddleja*.

Garden performance:

Plants of the new *Buddleja* have been observed to have good garden performance and tolerate rain, wind and temperatures ranging from about −15° C. to about 38° C.

It is claimed:

1. A new and distinct *Buddleja* plant named 'Burncross' as illustrated and described.

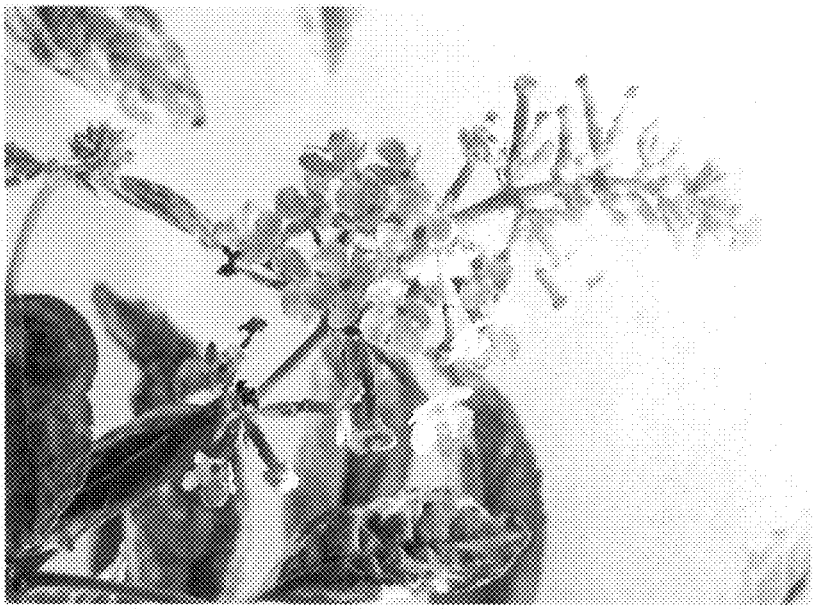
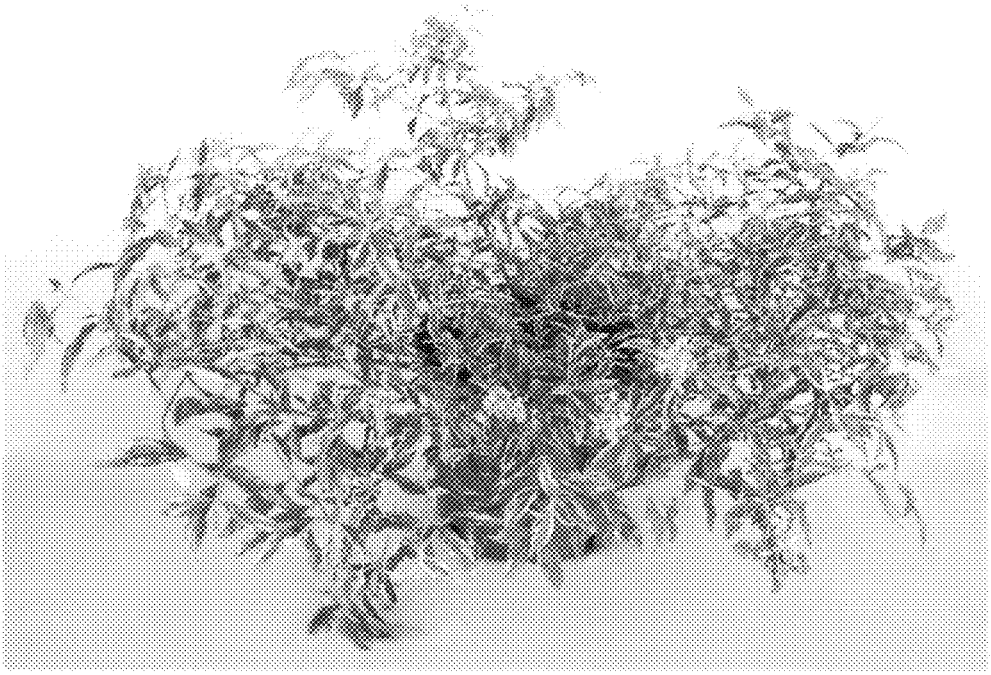

* * * * *